US009974429B2

(12) United States Patent
Smith et al.

(10) Patent No.: US 9,974,429 B2
(45) Date of Patent: May 22, 2018

(54) ARTICULATION SECTION WITH LOCKING

(71) Applicant: Boston Scientific Scimed, Inc., Maple Grove, MN (US)

(72) Inventors: Paul Smith, Smithfield, RI (US); John B. Golden, Norton, MA (US); Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 181 days.

(21) Appl. No.: 14/927,917

(22) Filed: Oct. 30, 2015

(65) Prior Publication Data
US 2016/0045097 A1 Feb. 18, 2016

Related U.S. Application Data

(63) Continuation of application No. 13/360,010, filed on Jan. 27, 2012, now Pat. No. 9,198,561.
(Continued)

(51) Int. Cl.
*F16L 11/18* (2006.01)
*A61B 1/005* (2006.01)
(Continued)

(52) U.S. Cl.
CPC .......... *A61B 1/0057* (2013.01); *A61B 1/0055* (2013.01); *A61M 25/0043* (2013.01); *A61M 25/0147* (2013.01); *A61M 2025/015* (2013.01)

(58) Field of Classification Search
USPC .................. 138/119, 120; 600/141, 142, 149
See application file for complete search history.

(56) References Cited

U.S. PATENT DOCUMENTS 3,631,848 A    1/1972  Muller
4,108,211 A  * 8/1978  Tanaka ................. A61B 1/0055
                                                        138/120
(Continued)

FOREIGN PATENT DOCUMENTS

DE    42 28 459 A1    3/1994
DE    100 52 679 A1   5/2001
(Continued)

OTHER PUBLICATIONS

International Preliminary Report on Patentability for PCT application PCT/US2012/022833, dated Aug. 15, 2013, 6 pages.
(Continued)

*Primary Examiner* — James Hook
(74) *Attorney, Agent, or Firm* — Bookoff McAndrews, PLLC

(57) ABSTRACT

This invention is directed to a flexible device having a longitudinal axis, a first elongate member configured to move the flexible device in a first direction relative to the longitudinal axis, and a second elongate member configured to move the flexible device in a second direction relative to the longitudinal axis that is different to the first direction. The flexible device can also have an articulation section including a plurality of articulation links, wherein at least one of the plurality of articulation links can include a body configured to receive the first elongate member and the second elongate member. The flexible device can also include a cinching element configured to engage the first elongate member to substantially limit movement between the plurality of articulation links when a tensile force is applied to the first elongate member and configured to disengage the first elongate member to permit movement between the plurality of articulation links when a tensile force is applied to the second elongate member.

10 Claims, 6 Drawing Sheets

Related U.S. Application Data

(60) Provisional application No. 61/438,143, filed on Jan. 31, 2011.

(51) Int. Cl.
*A61M 25/00* (2006.01)
*A61M 25/01* (2006.01)

(56) References Cited

U.S. PATENT DOCUMENTS

| | | | |
|---|---|---|---|
| 4,432,349 A * | 2/1984 | Oshiro | A61B 1/0055 138/120 |
| 4,601,283 A | 7/1986 | Chikama | |
| 4,790,294 A | 12/1988 | Allred et al. | |
| 5,005,558 A * | 4/1991 | Aomori | A61B 1/0055 600/141 |
| 5,251,611 A | 10/1993 | Zehel et al. | |
| 5,325,845 A | 7/1994 | Adair | |
| 5,345,937 A | 9/1994 | Middleman et al. | |
| 5,383,849 A | 1/1995 | Johlin, Jr. | |
| 5,402,793 A | 4/1995 | Gruner et al. | |
| 5,501,654 A | 3/1996 | Failla et al. | |
| 5,556,370 A | 9/1996 | Maynard | |
| 5,704,898 A * | 1/1998 | Kokish | A61B 1/0052 600/139 |
| 5,749,602 A | 5/1998 | Delaney et al. | |
| 5,749,828 A | 5/1998 | Solomon et al. | |
| 5,759,151 A | 6/1998 | Sturges | |
| 5,865,378 A | 2/1999 | Hollinshead et al. | |
| 5,916,146 A | 6/1999 | Allota et al. | |
| 5,916,147 A | 6/1999 | Boury | |
| 5,997,047 A | 12/1999 | Pimentel et al. | |
| 6,013,024 A | 1/2000 | Mitsuda et al. | |
| 6,491,626 B1 * | 12/2002 | Stone | A61B 1/00 403/291 |
| 6,610,007 B2 | 8/2003 | Belson et al. | |
| 6,626,210 B2 | 9/2003 | Luettgen et al. | |
| 6,629,651 B1 | 10/2003 | Male et al. | |
| 6,749,560 B1 | 6/2004 | Konstorum et al. | |
| 6,790,173 B2 | 9/2004 | Saadat et al. | |
| 6,858,024 B1 | 2/2005 | Berg et al. | |
| 6,899,673 B2 | 5/2005 | Ogura et al. | |
| 7,066,411 B2 | 6/2006 | Male et al. | |
| 7,337,808 B2 | 3/2008 | Shamir et al. | |
| 7,338,505 B2 | 3/2008 | Belson | |
| 7,410,483 B2 | 8/2008 | Danitz et al. | |
| 7,533,906 B2 | 5/2009 | Luettgen et al. | |
| 7,682,319 B2 | 3/2010 | Martin et al. | |
| 8,777,843 B2 * | 7/2014 | Banju | A61B 1/0055 600/141 |
| 8,900,267 B2 * | 12/2014 | Woolfson | A61B 17/0218 600/141 |
| 2002/0032371 A1 * | 3/2002 | Torii | A61B 1/0052 600/142 |
| 2002/0068868 A1 | 6/2002 | Thompson et al. | |
| 2002/0177750 A1 | 11/2002 | Pilvisto | |
| 2003/0023142 A1 | 1/2003 | Grabover et al. | |
| 2004/0193008 A1 | 9/2004 | Jaffe et al. | |
| 2004/0199052 A1 | 10/2004 | Banik et al. | |
| 2004/0236316 A1 | 11/2004 | Danitz et al. | |
| 2005/0056333 A1 | 3/2005 | Utaki | |
| 2005/0075538 A1 | 4/2005 | Banik et al. | |
| 2005/0096694 A1 | 5/2005 | Lee | |
| 2005/0103903 A1 | 5/2005 | Shamir et al. | |
| 2005/0154261 A1 | 7/2005 | Ohline et al. | |
| 2005/0273084 A1 | 12/2005 | Hinman et al. | |
| 2006/0111209 A1 | 5/2006 | Hinman et al. | |
| 2006/0111616 A1 | 5/2006 | Danitz | |
| 2006/0178560 A1 | 8/2006 | Saadat et al. | |
| 2006/0178562 A1 | 8/2006 | Saadat et al. | |
| 2007/0049800 A1 | 3/2007 | Boulais | |
| 2007/0219411 A1 | 9/2007 | Dejima et al. | |
| 2008/0091073 A1 | 4/2008 | Park | |
| 2008/0249364 A1 | 10/2008 | Korner | |
| 2008/0287741 A1 | 11/2008 | Ostrovsky et al. | |
| 2008/0287862 A1 | 11/2008 | Weitzner et al. | |
| 2009/0124857 A1 | 5/2009 | Viola | |
| 2010/0069715 A1 | 3/2010 | Perry | |
| 2010/0076266 A1 | 3/2010 | Boulais et al. | |
| 2010/0130924 A1 | 5/2010 | Martin et al. | |
| 2010/0261964 A1 | 10/2010 | Danitz et al. | |
| 2013/0090529 A1 * | 4/2013 | Boulais | A61B 1/0052 600/149 |

FOREIGN PATENT DOCUMENTS

| | | |
|---|---|---|
| DE | 103 08 902 A1 | 12/2003 |
| EP | 0 667 126 A1 | 8/1995 |
| EP | 1 977 677 A1 | 10/2008 |
| EP | 2 060 225 A1 | 5/2009 |
| EP | 2 100 547 A1 | 9/2009 |
| JP | 63-292935 A | 11/1988 |
| WO | WO 92/19147 A1 | 11/1992 |
| WO | WO 97/12557 A1 | 4/1997 |

OTHER PUBLICATIONS

International Search Report and Written Opinion issued in International Application No. PCT/US2012/022833, dated Mar. 23, 2012.

* cited by examiner

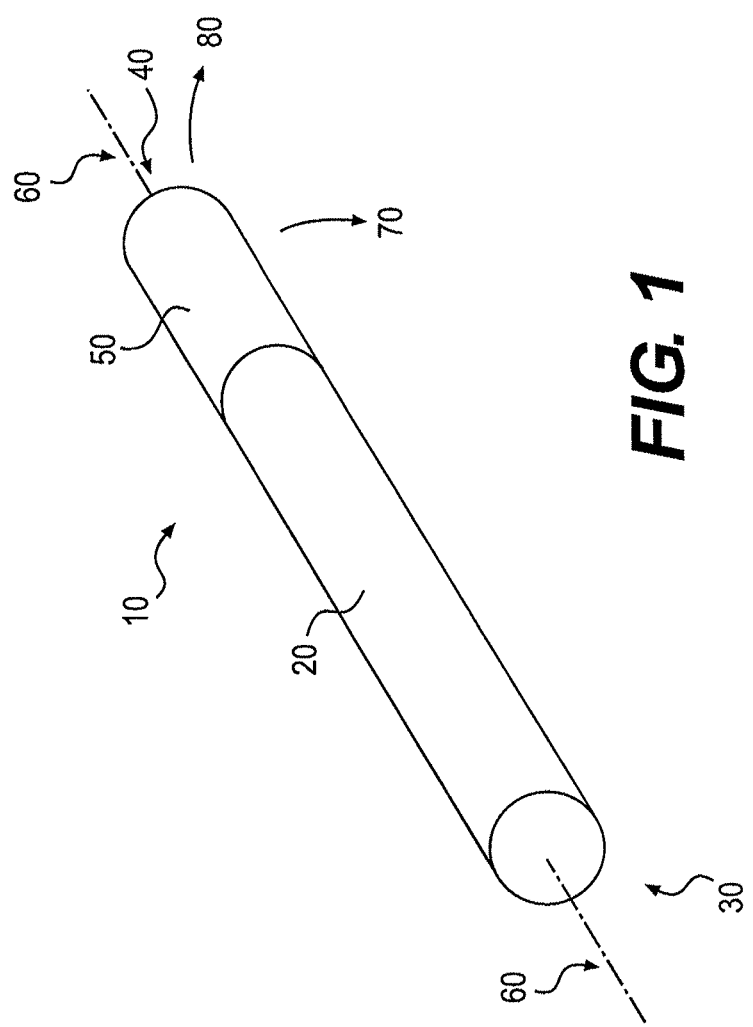

ARTICULATION SECTION WITH LOCKING

This application is a continuation of U.S. application Ser. No. 13/360,010, filed Jan. 27, 2012, now U.S. Pat. No. 9,198,561 B2, which claims the benefit of priority from U.S. Provisional Application No. 61/438,143, filed Jan. 31, 2011, all of which are incorporated herein by reference in their entireties.

FIELD OF THE INVENTION

Embodiments of the present invention relate to articulated medical devices. In particular, embodiments of the present invention include an articulation section with locking.

BACKGROUND OF THE INVENTION

Articulated medical devices provide access to sites within a patient's body that are difficult to reach using rigid non-articulating devices. An articulated endoscope can provide direct access to internal organs, and an articulated catheter may provide access to tortuous vascular structures. These articulated devices are flexible to provide easy manipulation. Once the medical device is positioned at the surgical site, it can be desirable to lock the device's shape. A locked device, for example, is better able to lift or retract tissue than a flexible one.

Traditional medical devices often lack the ability to efficiently lock and unlock. Most locks operate by compressing adjacent articulation links. However, significant compressive forces must be applied to lock a joint that is specifically designed for movement. These locks often apply high tensile forces to wires in the joint to ensure adequate compression of adjacent links.

SUMMARY OF THE INVENTION

The articulation sections described herein overcome at least some of the limitations of the prior art. In contrast to the prior art, embodiments of the current invention include, for example, an articulation section that can be locked using a single wire. The articulation section can also be unlocked by applying tension to another wire. The present disclosure is broadly applicable to various medical devices and other devices requiring articulation. For example, borescopes use articulation to access difficult-to-reach locations within engines or other industrial devices.

One aspect of the invention is directed to a flexible device having a longitudinal axis, a first elongate member configured to move the flexible device in a first direction relative to the longitudinal axis, and a second elongate member configured to move the flexible device in a second direction relative to the longitudinal axis that is different to the first direction. The flexible device can also have an articulation section including a plurality of articulation links, wherein at least one of the plurality of articulation links can include a body configured to receive the first elongate member and the second elongate member. The flexible device can also include a cinching element configured to engage the first elongate member to substantially limit movement between the plurality of articulation links when a tensile force is applied to the first elongate member and configured to disengage the first elongate member to permit movement between the plurality of articulation links when a tensile force is applied to the second elongate member.

According to another aspect, the invention can include a flexible device having a longitudinal axis and a first elongate member configured to move the flexible device in a first direction relative to the longitudinal axis, wherein part of the first elongate member can be located outside the flexible device. The flexible device can also include a second elongate member configured to move the flexible device in a second direction relative to the longitudinal axis that is different to the first direction and an articulation section having a side surface including a first aperture and a second aperture, wherein a first lumen extends between the first aperture and the second aperture. The flexible device can further include a cinching element located within the first lumen and configured to engage the first elongate member to substantially limit movement of the articulation section when a tensile force is applied to the first elongate member and configured to disengage the first elongate member to permit movement of the articulation section when a tensile force is applied to the second elongate member.

According to another aspect, the invention can include a flexible device having a longitudinal axis and a first elongate member configured to move the flexible device in a first direction relative to the longitudinal axis, wherein the first elongate member includes a first bead. The flexible device can also include a second elongate member configured to move the flexible device in a second direction relative to the longitudinal axis that is different to the first direction and an articulation section configured to move relative to the longitudinal axis by movement of the first elongate member and the second elongate member. Further, the flexible device can include a cinching element configured to engage the first bead to substantially limit movement of the articulation section and configured to disengage the first bead to permit movement of the articulation section.

Additional objects and advantages of the invention will be set forth in part in the description which follows, and in part will be obvious from the description, or may be learned by practice of the invention. The objects and advantages of the invention will be realized and attained by means of the elements and combinations particularly pointed out below.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 1 is a perspective view of a device, according to an exemplary embodiment of the invention;

DESCRIPTION OF THE EMBODIMENTS

Figure 2B:
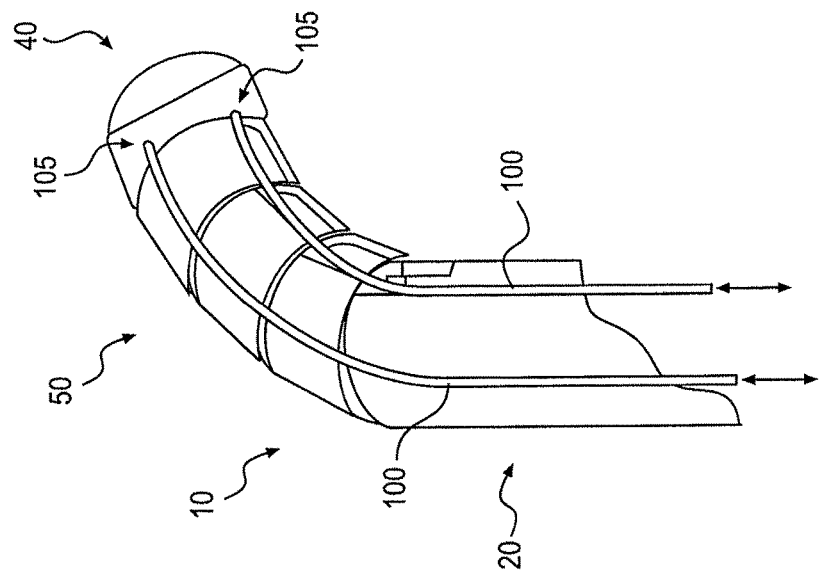
FIG. 2B is a cut-away side view of the articulation section as shown in FIG. 2A, according to an exemplary embodiment of the invention.

Reference will now be made to exemplary embodiments of the invention, examples of which are illustrated in the accompanying drawings. Wherever possible, the same reference numbers will be used throughout the drawings to refer to the same or like parts.

FIG. 1 depicts a device 10, according to an exemplary embodiment. Device 10 can include a medical device configured for use with a surgical method, including a therapeutic or diagnostic procedure. Device 10 can include an endoscope, a guide tube, a catheter, a guidewire, or other type of elongate medical device. For example, device 10 may be used for procedures within or adjacent to various body organs, such as, an esophagus, a heart, a stomach, a pelvic area, a bladder, an intestine, or a gastrointestinal, urinary, or pulmonary tract.

Device 10 may be configured for insertion into a patient's body through an anatomical opening. In other embodiments, device 10 may be used in natural orifice transluminal endoscopic surgery (NOTES) procedures or single incision laparoscopic surgical (SILS) procedures. Accordingly, device 10 can be shaped and sized for placement into a patient via a body cavity or an incision.

Device 10 can be configured to operate with one or more instruments (not shown) used in various surgical procedures. For example, device 10 can include one or more lumens (not shown) configured to receive a grasper, a pair of scissors, a hook, an ablation device, or other type of surgical instrument. Device 10 may also be configured to operate with, or include, insufflation, irrigation, suction, imaging, or systems used in endoscopic, laparoscopic, or other surgical procedures.

Device 10 can include a shaft 20 having a proximal end 30 and a distal end 40. Proximal end 30 can be manipulated by an operator to control distal end 40. For example, proximal end 30 can include one or more knobs, handles, or other devices (not shown) configured to move distal end 40 relative to proximal end 30.

Shaft 20 can also include an articulation section 50. As shown in FIG. 1, articulation section 50 can be located at or near distal end 40. In other embodiments, articulation section 50 can be located anywhere along shaft 20, or encompass the entire length of shaft 20. In operation, an operator can manipulate articulation section 50 to move distal end 40 in any direction. For example, device 10 can be moved in a first direction 70 relative to longitudinal axis 60 and in a second direction 80 relative to longitudinal axis 60 that is different to first direction 70.

Figure 2A:
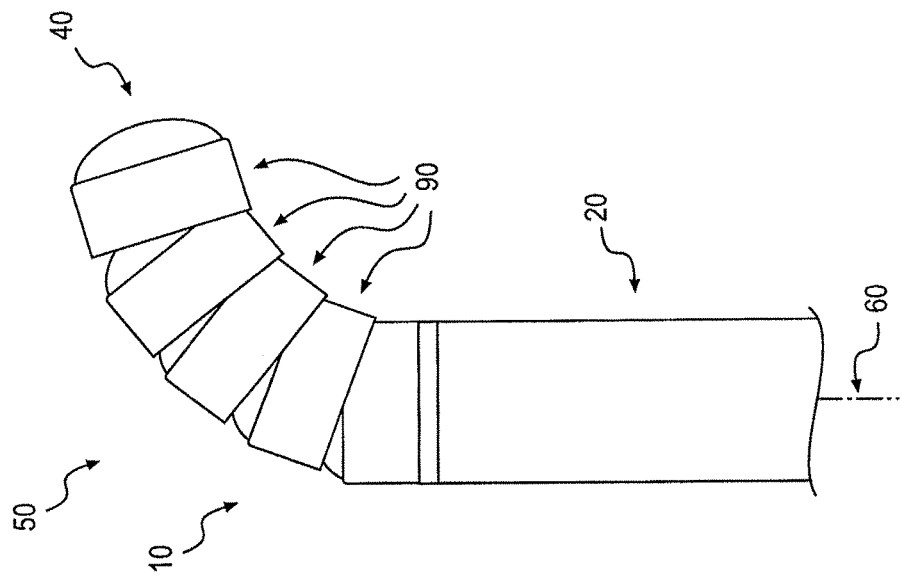
FIG. 2A is a side view of an articulation section, according to an exemplary embodiment of the invention.

FIG. 2A depicts articulation section 50 curving to the right and including several articulation links 90. Any number of articulation links 90 may be configured to move relative to each other to move articulation section 50 in one or more directions relative to longitudinal axis 60. Various articulation links 90 are known in the art and could be used as described herein.

FIG. 2B depicts a cut away view of device 10 as shown in FIG. 2A. Two elongate members 100 are shown extending through at least part of articulation section 50. Elongate members 100 can be moved distally or proximally to move articulation section 50. For example, a tensile force may be applied to a single elongate member 100 to curve articulation section 50. One or more elongate members 100 may be moved to control movement of articulation section 50 in one or more directions.

Elongate members 100 can include a cable, a wire, a ribbon, or other type of elongate element configured to transfer a movement or a mechanical force. Elongate members 100 can be configured to transfer tensile force, compressive force, or both tensile and compressive forces. For example, elongate members 100 could include a metal alloy, braided synthetic thread, or similar flexible material configured to transfer a tensile force.

Elongate members 100 may be sized and shaped depending on load requirements and geometric constraints. Also, part of elongate member 100 may be fixedly attached to part of articulation section 50. For example, a distal end 105 of elongate member 100 may be fixedly attached to distal end 40.

In operation, articulation section 50 may be moved to a curved configuration and locked. For example, articulation section 50 could be locked in the curved configuration as shown in FIGS. 2A and 2B. As explained below, one or more elongate members 100 may be locked relative to one or more articulation links 90. Other elongate members 100 may be moved to unlock articulation section 50.

Figure 3:
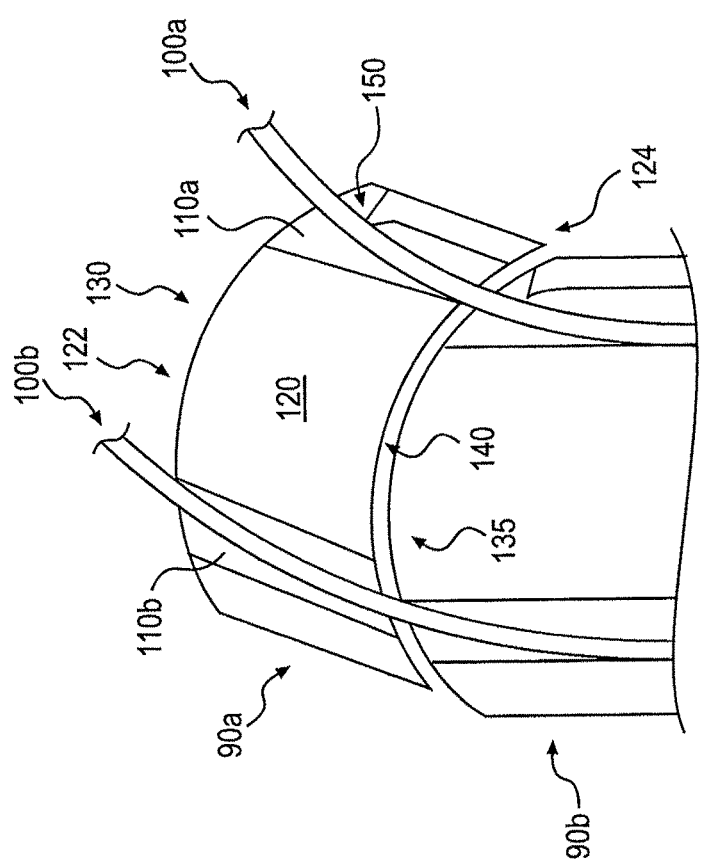
FIG. 3 is a cut-away side view of an articulation section, according to an exemplary embodiment of the invention.

FIG. 3 shows an articulation link 90a, according to an exemplary embodiment. Articulation link 90a can include a body 120. Body 120 can have a substantially cylindrical shape and a generally circular cross-section. In other embodiments, body 120 can have a different shape or cross-section, and may be shaped and sized as required.

Body 120 can be formed from one or more materials, such as, for example, a metal alloy, a polymer, a ceramic, or combination thereof. One or more external surfaces of body 120 may be treated to enhance lubricity, friction, hardness, strength, or another physical parameter. All or part of body 120 may be coated with various materials to improve these and other physical parameters.

Body 120 can include a first contact surface 130 and a second contact surface 140. First contact surface 130 can be located proximate a first end 122 of body 120 and second contact surface 140 can be located proximate a second end 124 of body 120 opposite first end 122. Also, first contact surface 130 can be located generally distally and second contact surface 140 can be located generally proximally. In some instances, first contact surface 130 can be the distal-most surface and second contact surface 140 can be the proximal-most surface of body 120.

Surfaces 130, 140 can be generally flat, curved, or shaped as required to permit movement between adjacent articulation links 90. For example, second surface 140 can be configured to engage a first surface 135 of an adjacent articulation link 90b. Engagement of surfaces 140, 135 can permit relative movement between articulation links 90a, 90b to permit movement of articulation section 50.

In some embodiments, articulation link 90a can include a first lumen 110a configured to receive a first elongate member 100a and a second lumen 110b configured to receive a second elongate member 100b. In other embodiments, articulation link 90a could include one or more lumens 110. Lumens 110 can be shaped and sized as required, and may extend from first surface 130 to second surface 140.

Device 10 can also include a cinching element 150. Cinching element 150 can be configured to substantially limit movement of articulation section 50. In particular, cinching element 150 can be configured to engage one or more elongate members 100 to at least partially limit movement of the one or more elongate members 100 relative to articulation section 50. Cinching element 150 may be configured to provide a frictional force to restrict movement of elongate member 100. In some embodiments, cinching element 150 may be configured to apply a lateral force or a medial force to elongate member 100 to partially restrict its movement.

Cinching element 150 can be located within device 10. For example, cinching element 150 can be located at or near a proximal end of articulation section 50 or at or near a distal end of shaft 20. One or more articulation links 90 can include one or more cinching elements 150.

Cinching element 150 could include a sharp edge, a serration, a roughened surface, small kinks, an arcuate surface, a protrusion, or other structure configured to engage elongate member 100a. Similarly, elongate member 100 could include a feature configured to engage cinching element 150. Cinching element 150 may be specifically designed to engage a particular type of elongate member 100a. For example, a nylon elongate member 100a may require a serrated cinching element 150 while a steel elongate member 100a may require cinching element 150 to have a sharp edge.

In use, articulation section 50 may be curved by applying tension to elongate member 100a. As articulation section 50 is curved, cinching element 150 may engage elongate member 100a. Such engagement may act to limit the relative movement between articulation link 90a and elongate member 100a. Multiple articulation links 90 can each include one or more cinching elements 150 configured to similarly engage elongate member 100a. Engaging elongate member 100a at multiple locations can transfer multiple frictional forces between articulation links 90 and elongate member 100a. These forces can be applied laterally and/or medially to a longitudinal axis of elongate member 100a. The cumulative application of these frictional forces along elongate member 100a can provide secure locking of articulation section 50.

Cinching element 150 can also be configured to disengage elongate member 100a to unlock articulation section 50. In some embodiments, a tensile force can be applied to elongate member 100b. Elongate member 100b and second lumen 110b can be located generally opposite first lumen 110a. This tensile force can act to at least partially straighten articulation section 50 to move it from its curved configuration. The straightening can also function to disengage cinching elements 150 from elongate member 100a. In other embodiments, other types of lateral or medial movement can function to disengage one or more cinching elements 150.

Figure 4:
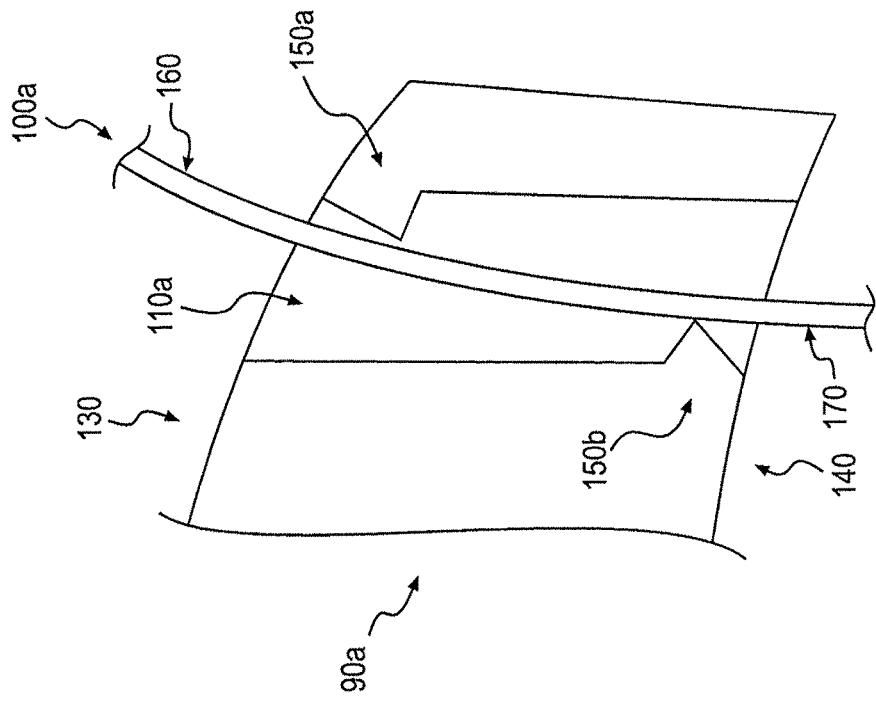
FIG. 4 is a cut-away side view of an articulation link as shown in FIG. 3, according to an exemplary embodiment of the invention.

Articulation link 90a can include multiple cinching elements 150. For example, FIG. 4 shows a first cinching element 150a located distally and a second cinching element 150b located proximally within lumen 110a. Cinching elements 150a, 150b can be positioned to engage one or more sides of elongate member 100a. As shown in FIG. 4, first cinching element 150a could be located laterally to first elongate member 100a to engage a lateral surface 160 of elongate member 100a. Also, second cinching element 150b could be located medial to first elongate member 100a to engage a medial surface 170 of elongate member 100a.

Figure 5B:
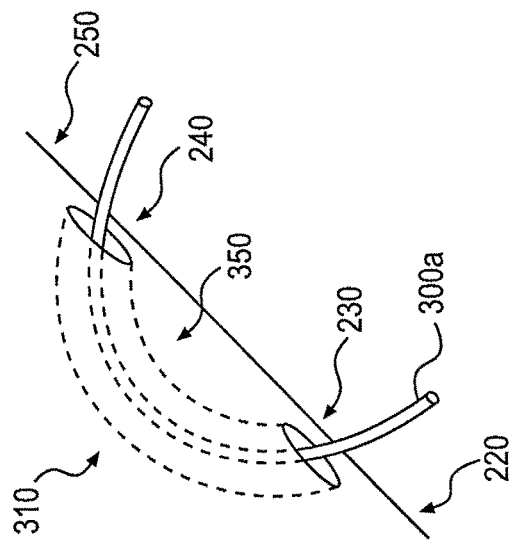
FIG. 5B is an enlarged side view of the articulation section as shown in FIG. 5A, according to another exemplary embodiment of the invention.
Figure 5A:
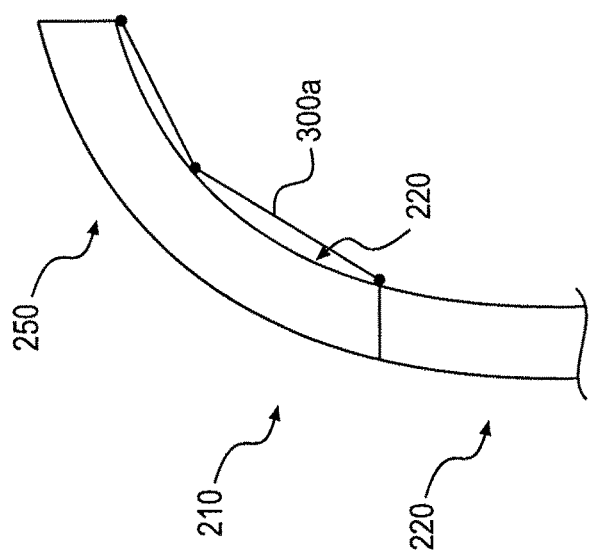
FIG. 5A is a side view of an articulation section, according to another exemplary embodiment of the invention.

FIGS. 5A and 5B depict a device 210 according to another exemplary embodiment. Device 210 can include an articulation section 250, a shaft 220, and an elongate member 300a. Part of elongate member 300a can be located outside articulation section 250. In some embodiments, elongate member 300a can lie substantially parallel to a side surface 220 of articulation section 250.

Similar to the previous embodiment, one or more elongate members 300a can be moved to move articulation section 250. Elongate member 300a may move articulation section 150 to lock articulation section 250 in a curved position. Another elongate member (not shown) can be moved to unlock articulation section 250.

FIG. 5B shows an enlarged view of articulation section 250. Articulation section 250 can include side surface 220 having a first aperture 230 and a second aperture 240. A lumen 310 within articulation section 250 can extend between first aperture 230 and second aperture 240. Apertures 230, 240 can be variously located along articulation section 250.

A cinching element 350 can be located within lumen 310 and configured to engage elongate member 300a. One or more cinching elements 350 can be curved. In some embodiments, one or more cinching elements 150 could be provided within lumen 310.

Cinching of elongate member 300a can occur due to a tortuous path that elongate member 300a takes within lumen 310. The tortuous path can apply frictional forces to elongate member 300a when articulation section 250 is in a curved configuration. One or more cinching elements 350 could be configured to apply frictional forces to elongate member 300a.

It is also possible that one or more parts of elongate member 300a external to articulation section 250 could be subjected to frictional forces. For example, one or more cinching elements 350 located on side surface 220 could be configured to engage parts of elongate member 300a lying outside lumen 310. As previously described, frictional forces applied to elongate member 300a can be engaged and disengaged to lock and unlock articulation section 250. Also, elongate member 300a may have one or more features configured to engage cinching element 350.

Figure 6B:
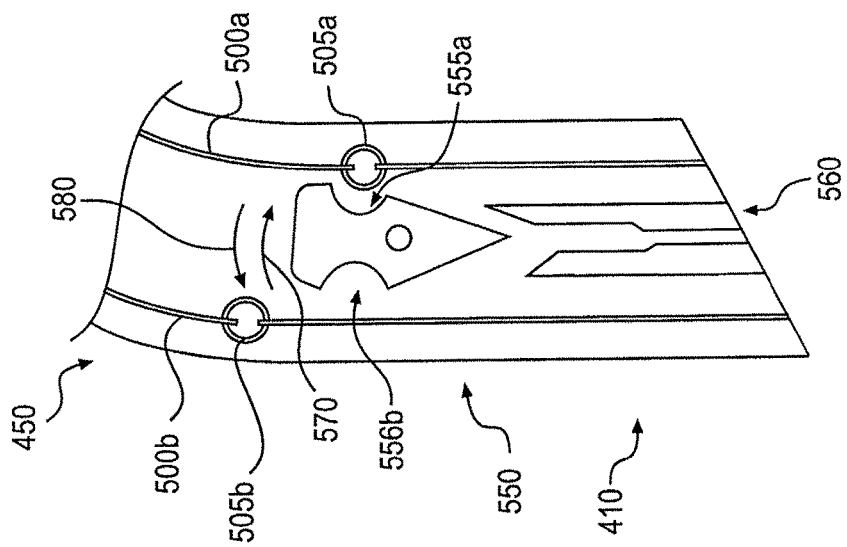
FIG. 6B is an enlarged cut-away side view of the articulation section as shown in FIG. 6A, according to another exemplary embodiment of the invention.
Figure 6A:
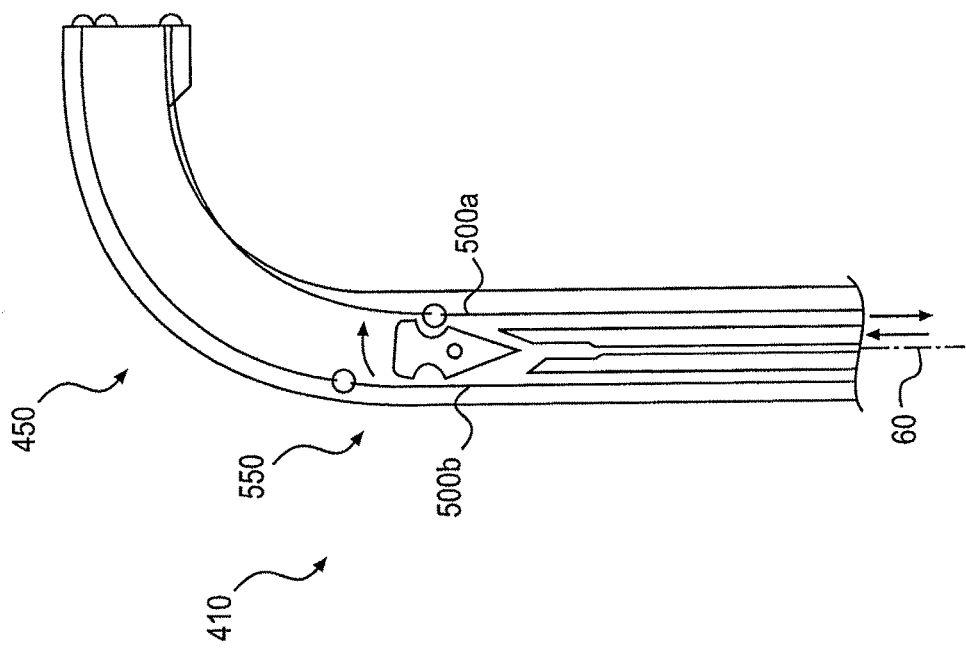
FIG. 6A is a cut-away side view of an articulation section, according to another exemplary embodiment of the invention.

FIGS. 6A and 6B depict a device 410 containing another type of a cinching element 550. FIG. 6A shows device 410 including an articulation section 450 and elongate members 500a, 500b. Similar to the previous embodiments, one or more elongate members 500 can be moved to move, lock, and unlock articulation section 450.

Cinching element 550 can be configured to releasably engage a bead 505a located on elongate member 500a. In particular, cinching element 550 can include a first detent 555a configured to engage first bead 505a. Bead 505 can also include a ring, a solid or hollow sphere, or other type of protrusion on elongate member 500. Bead 505a and detent 555a can be any shape and size to limit relative movement of cinching element 550 and elongate member 500. Specifically, engaging detent 555a and first bead 505a can limit movement of elongate member 500a to substantially limit the movement of articulation section 450.

In some embodiments, cinching element 550 can be moveably coupled to device 410. As shown in FIGS. 6A and 6B, cinching element 550 can be pivotally mounted within device 410. Other moveable couplings are also contemplated. For example, rather than move by pivoting, cinching element 550 may bend to engage bead 505.

To move cinching element 550, device 410 can include one or more control members 560. Control members 560 can include any device configured to move cinching member 550. For example, control members 560 could include a cable, wire, or other type of elongate member configured to transmit a force or a movement.

Cinching element 550 can be configured to move in a first direction 570 to engage first bead 505a, as shown in FIG. 6B. Such movement can substantially limit movement of articulation section 450 by limiting the movement of elongate member 500a. Cinching element 550 can also be configured to move opposite to the first direction to disengage first bead 505a. This movement could disengage cinching element 550 from first bead 505a to permit movement of elongate member 500a and articulation section 450.

Cinching element 550 can include one or more detents 555 configured to engage one or more beads 505. In some embodiments, cinching element 550 can include a second detent 555b configured to engage a second bead 505b located on a second elongate member 500b. Cinching element 550 could be moved to engage second bead 505b to lock articulation section 450 in another curved configuration. For example, cinching element 550 could move in a second direction 580 to engage second bead 505b to limit movement of elongate member 500b. Similar to engaging and disengaging first bead 505a, second bead 505b could be engaged and disengaged to substantially lock and unlock movement of articulation section 450.

It is also contemplated that each elongate member 500 could include more than one bead 505. Also, cinching element 550 could include more than one detent 555 configured to engage bead 505. Multiple beads 505 or multiple detents 555 can permit engagement between cinching element 550 and elongate member 500 at various positions along elongate member 500. Such multiple positioning can allow articulation section 450 to be locked at multiple angles. For example, articulation section 450 could be locked at 30, 45, or 60 degrees relative to longitudinal axis 60.

Following locking of articulation section 450 by engaging first bead 505a and first detent 555a, second bead 505b could be configured to unlock articulation section 450. For example, proximal movement of second bead 505b relative to cinching element 550 could cause second bead 505b to engage cinching element 550. This engagement could cause cinching element 550 to move opposite first direction 570, as previously described. Such movement could disengage first bead 505a and cinching element 550 to permit movement of elongate member 500a and articulation section 450.

Figure 7:
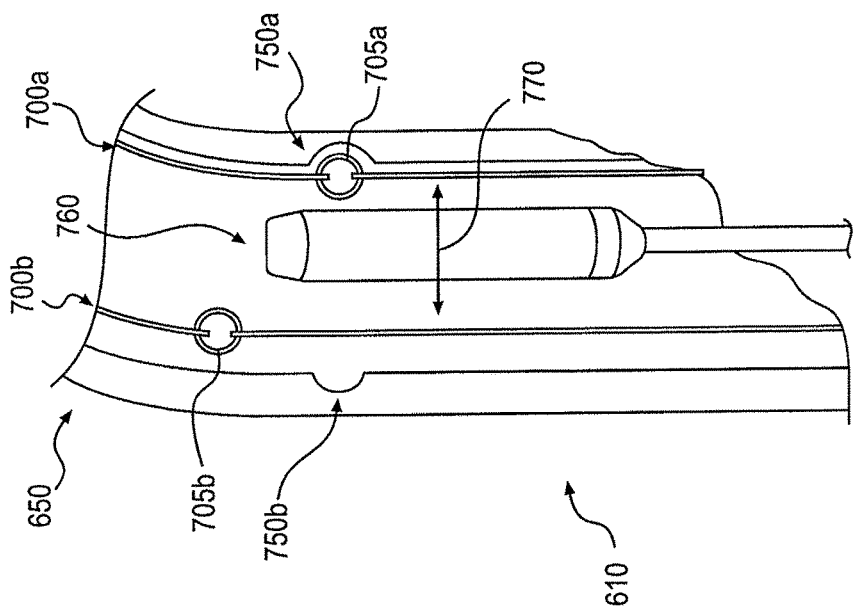
FIG. 7 is a cut-away side view of an articulation section, according to another exemplary embodiment of the invention.

FIG. 7 depicts an articulation section 650, according to another exemplary embodiment. Articulation section 650 can include a cinching element 750a fixedly coupled to a device 610. Cinching element 750a can be located lateral to a first elongate member 700a. A controller 760 mounted within device 610 can be configured to move one or more beads 705a, 705b located on elongate members 700a, 700b, respectively. For example, controller 760 can be configured to expand laterally, as shown by an arrow 770. Lateral movement of controller 760 can cause lateral movement of first bead 705a such that first bead 705a can engage cinching element 750a. As previously described, such engagement can substantially limit movement of articulation section 650. Medial movement of controller 760 can unlock articulation section 650. Lateral movement may also be achieved by twisting controller 760 to urge bead 705 into cinching element 750. Such a controller may require a non-circular cross-section.

Controller 760 can include any type of device configured to provide lateral or medial movement of one or more beads 705. For example, controller 760 could include an inflatable balloon, a shape memory alloy, a lever, a gear, a wedge, or other device configured to permit lateral or medial movement. Controller 760 may be configured to move first bead 705a to engage first bead 705a and cinching element 750a to substantially limit movement of articulation section 650.

As with the previous embodiment, controller 760 may be configured to move a second bead 705b to engage and disengage a second cinching element 750b fixedly coupled to endoscope 710. Controller 760 can also be configured to move one or more beads 705 to engage cinching element 705 having one or more detents, to lock articulation section 650 at multiple angles, as previously described. Other aspects of the previous embodiments may also be combined with controller 760.

The embodiments described herein are exemplary only, and it will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. A flexible device having a longitudinal axis, comprising:
   a first elongate member configured to move a portion of the flexible device in a first direction relative to the longitudinal axis, wherein a first portion of the first elongate member extends along an outer surface of the flexible device;
   a second elongate member configured to move the portion of the flexible device in a second direction relative to the longitudinal axis, wherein the second direction is different from the first direction;
   an articulation section having a side surface including a first aperture and a second aperture, wherein a first lumen extends between the first aperture and the second aperture, and a second portion of the first elongate member extends through the first lumen; and
   a plurality of cinching elements located within the first lumen, wherein the plurality of cinching elements are configured to:
   (a) engage different sides of the first elongate member to limit movement of the articulation section when a first tensile force is applied to the first elongate member, and
   (b) disengage from the first elongate member to permit movement of the articulation section when a second tensile force is applied to the second elongate member.

2. The flexible device of claim 1, wherein at least one of the plurality of cinching elements includes at least one of a sharp edge and a serrated surface for engaging and disengaging from the second portion of the first elongate member.

3. A flexible device, comprising:
   a shaft including a distal articulation section, wherein the distal articulation section has a side surface including a first aperture and a second aperture, and a lumen that extends between the first aperture and the second aperture;
   an elongate member configured to deflect the distal articulation section, wherein a first portion of the elongate member extends from outside of the distal articulation section into the first aperture, a second portion of the elongate member extends through the lumen within the distal articulation section, and a third portion of the elongate member extends out of the distal articulation section from the second aperture; and a plurality of cinching elements located within the lumen, wherein the plurality of cinching elements are configured to engage different sides of the second portion of the elongate member to limit movement of the distal articulation section when a tensile force is applied to the elongate member.

4. The flexible device of claim 3, wherein at least one cinching element of the plurality of cinching elements includes at least one of a sharp edge and a serrated surface for contacting the elongate member to limit movement of the distal articulation section.

5. The flexible device of claim 3, wherein the lumen is a first lumen, and the side surface further includes a third aperture that opens into a second lumen.

6. The flexible device of claim 5, wherein the third portion of the elongate member extends from outside of the distal articulation section into the third aperture, and a fourth portion of the elongate member extends through the second lumen within the distal articulation section.

7. The flexible device of claim 5, wherein the side surface further includes a fourth aperture, and the second lumen extends between the third aperture and the fourth aperture.

8. The flexible device of claim 7, wherein the third portion of the elongate member extends from outside of the distal articulation section into the third aperture, a fourth portion of the elongate member extends through the second lumen within the distal articulation section, and a fifth portion of the elongate member extends out of the distal articulation section from the fourth aperture.

9. The flexible device of claim 3, wherein the lumen is curved.

10. The flexible device of claim 3, wherein the plurality of cinching elements includes a plurality of first cinching elements, the flexible device further includes a second cinching element on the side surface, and the second cinching element is configured to engage one of the first portion and the third portion of the elongate member to limit movement of the distal articulation section when the tensile force is applied to the elongate member.

* * * * *